(12) United States Patent
Cahalon et al.

(10) Patent No.: US 7,285,536 B2
(45) Date of Patent: Oct. 23, 2007

(54) ANTI-CANCER THERAPEUTIC COMPOUNDS

(75) Inventors: Liora Cahalon, Givataim (IL); Irun R. Cohen, Rehovot (IL); Ofer Lider, Kfar Bilu Bet (IL); Raanan Margalit, Ganei Yochanan (IL)

(73) Assignee: Yeda Research and Development Co., Ltd., Rechovot (IL)

( * ) Notice: Subject to any disclaimer, the term of this patent is extended or adjusted under 35 U.S.C. 154(b) by 182 days.

(21) Appl. No.: 10/002,145

(22) Filed: Dec. 5, 2001

(65) Prior Publication Data

US 2003/0130230 A1    Jul. 10, 2003

(51) Int. Cl.
*A61K 31/70* (2006.01)

(52) U.S. Cl. ........................................ 514/25
(58) Field of Classification Search .................. 514/25
See application file for complete search history.

(56) References Cited

U.S. PATENT DOCUMENTS

| 1,950,100 A | 6/1934 | Crandall |
| 4,401,662 A | 8/1983 | Lormeau et al. |

(Continued)

FOREIGN PATENT DOCUMENTS

EP    0114589    1/1984

(Continued)

OTHER PUBLICATIONS

Timar et al., Invasion Metastasis, 1990;10:301-305.*

(Continued)

*Primary Examiner*—San-Ming Hui

(57) ABSTRACT

A treatment for cancer, and in particular, of therapeutic compounds which block the ability of cytokines and chemokines to promote metastasis of malignant cells. The therapeutic compound comprises a carboxylated and/or sulfated oligosaccharide, preferably in a substantially purified form, which is a heparin or heparan-sulfate derived saccharide compound. In one embodiment of the present invention, the carbohydrate or oligosaccharide has a molecular weight of no more than about 3000 daltons, preferably lying in the range of about 400 to about 2000 daltons, most preferably between about 400 and about 1100 daltons. Generally, substances of the present invention inhibit tumor cell migration, as determined by biological assays, and comprise molecules of various sugar units of which the basic unit of activity is associated with a disaccharide. However, larger oligosaccharide chains of up to about 10 sugar units, containing the basic disaccharide unit of activity can also function to inhibit such activity.

28 Claims, 15 Drawing Sheets

U.S. PATENT DOCUMENTS

| | | | |
|---|---|---|---|
| 4,446,314 A | | 5/1984 | Jordan |
| 4,468,385 A | | 8/1984 | Callahan et al. |
| 4,539,398 A | | 9/1985 | Rosenberg |
| 4,607,025 A | | 8/1986 | Petitou et al. |
| 4,727,063 A | | 2/1988 | Naggi et al. |
| 4,774,231 A | | 9/1988 | Petitou et al. |
| 4,801,583 A | | 1/1989 | Petitou et al. |
| 4,818,816 A | | 4/1989 | Petitou et al. |
| 4,882,318 A | * | 11/1989 | Vlodavsky et al. ............ 514/56 |
| 4,889,808 A | | 12/1989 | Rappaport |
| 4,933,326 A | | 6/1990 | Bianchini et al. |
| 4,943,630 A | | 7/1990 | Jacquinet et al. |
| 4,973,580 A | | 11/1990 | Mascellani et al. |
| 4,981,955 A | | 1/1991 | Lopez |
| 4,987,223 A | | 1/1991 | Choay et al. |
| 4,990,502 A | | 2/1991 | Lormeau et al. |
| 5,010,063 A | | 4/1991 | Piani et al. |
| 5,034,520 A | | 7/1991 | Lormeau et al. |
| 5,474,987 A | | 12/1995 | Cohen et al. |
| 5,580,858 A | | 12/1996 | Ippolito et al. |
| 5,686,431 A | | 11/1997 | Cohen et al. |
| 5,861,382 A | | 1/1999 | Cohen et al. |
| 5,908,837 A | | 6/1999 | Cohen et al. |
| 6,020,323 A | | 2/2000 | Cohen et al. |
| 6,750,207 B1 | | 6/2004 | Cohen et al. |
| 2004/0198697 A1 | | 10/2004 | Cohen et al. |

FOREIGN PATENT DOCUMENTS

| | | |
|---|---|---|
| EP | 0375976 | 4/1990 |
| EP | 0394971 | 10/1990 |
| EP | 0669827 | 5/2001 |
| WO | PCT WO 88/05301 | 7/1988 |
| WO | PCT WO 89/05645 | 6/1989 |
| WO | PCT WO 90/03791 | 4/1990 |
| WO | PCT WO 94/11006 | 5/1994 |
| WO | PCT WO 03/047501 | 6/2003 |

OTHER PUBLICATIONS

Vlodavsky et al., Adv. Exp. Med. Biol., 992;13:317-327.*
Oligossacharide in Chemical Dictionary, 5th ed., McGraw-Hill, 1987.*
Timar et al. "Interactions of Exogenous Heparan Sulfate with Tumor Cells of Different Metastatic Phenotype", Invasion Metastasis, 10: 301-315, 1990.
Murdoch et al. "Chemokine Receptors and Their Role in Inflammation and Infectious Diseases", Blood, 95(10): 3032-3043, 2000.
Oberlin et al. "The CXC Chemokine SDF-1 Is the Ligand for LESTR/Fusin and Prevents Infection by T-Cell-Line-Adapted HIV-1", Nature, 382: 833-835, 1996.
Nagasawa et al. "Defects of B-Cell Lymphopoiesis and Bone-Marrow Myelopoiesis in Mice Lacking the CXC Chemokine PBSF/SDF-1", Nature, 382: 635-638, 1996.
McGrath et al. "Embryonic Expression and Function of the Chemokine SDF-1 and Its Receptor, CXCR4", Developmental Biology, 213: 442-456, 1999.
Ponomaryov et al. "Induction of the Chemokine Stromal-Derived Factor-1 Following DNA Damage Improves Human Stem Cell Function", The Journal of Clinical Investigation, 106(11): 1331-1339, 2000.
Gonzalo et al. "Critical Involvement of the Chemotactic Axis CXCR4/Stromal Cell-Derived Factor-1α in the Inflammatory Component of Allergic Airway Disease", The Journal of Immunology, 165: 499-508, 2000.
Peled et al. "The Chemokine SDF-1 Stimulates Integrin-Mediated Arrest of CD34+ Cells on Vascular Endothelium Under Shear Flow", The Journal of Clinical Investigation, 104(9): 1199-1211, 1999.
Peled et al. "Dependence of Human Stem Cell Engraftment and Repopulation of NOD/SCID Mice on CXCR4", Science, 283: 845-848, 1999.
Sawada et al. "Disturbed CD4+ T Cell Homeostasis and In Vitro HIV-1 Susceptibily in Transgenic Mice Expressing T Cell Line-Tropic HIV-1 Receptors", Journal of Experimental Medicine, 187(9): 1439-1449, 1998.
Aiuti et al. "The Chemokine SDF-1 Is A Chemoattractant for Human CD34+ Hematopoietic Progenitor Cells and Provides A New Mechanism to Explain the Mobilization of CD34+ Progenitors to Peripheral Blood", Journal of Experimental Medicine, 185(1): 111-120, 1997.
Peled et al. "The Chemokine SDF-1 Activates the Integrins LFA-1, VLA-4, and VLA-5 on Immature Human CD34+ Cells: Role in Transendothelial/Stromal Migration and Engraftment of NOD/SCID Mice", Blood, 95(11): 3289-3296, 2000.
Edinger et al. "Noninvasive Assessment of Tumor Cell Proliferation in Animal Models", Neoplasia, 1(4): 303-310, 1999.
Contag et al. "Bioluminescent Indicators in Living Mammals", Nature Medicine, 4(2): 245-247, 1998.
Condiotti et al. "Effect of Interleukin-12 on Antitumor Activity of Human Umbilical Cord Blood and Bone Marrow Cytotoxic Cells", Experimental Hematology, 26: 571-579, 1998.
Chowers et al. "Disaccharides Derived From Heparin or Heparan Sulfate Regulate IL-8 and IL-1β Secretion by Intestinal Epithelial Cells", Gastroenterology, 120: 449-459, 2001.
Goodman et al. "Anticoagulant, Thrombolytic, and Antiplatelet Drugs", The Pharmacological Basis of Theapeutics, II(Chap.55): 1312-1315, 1992.
Vlodavsky et al. "Modulation of Neovascularization and Metastasis by Species of Heparin", Adv. Exp. Med. Biol., 13: 317-327, 1992.
Hershkoviz et al. "Disaccharides Generated From Heparan Sulphate or Heparin Modulate Chemokine-Induced T-Cell Adhesion to Extracellular Matrix", Immunology, 99: 87-93, 2000.
Lider et al. "A Disaccharide That Inhibits Tumor Necrosis Factor α Is Formed From the Extracellular Matrix by the Enzyme Heparanase", Proc. Natl. Acad. Sci. USA, 92: 5037-5041, 1995.
Cahalon et al. "Heparin Disaccharides Inhibit Tumor Necrosis Factor-α Production by Macrophages and Arrest Immune Inflammation in Rodents", International Immunology, 9(10): 1517-1522, 1997.
Horvath et al. "Low Dose Heparin and Early Kidney Transplant Function", Australian and New Zealand Journal of Medicine, 5: 537-539, 1975.
Kariya et al. "Preparation of Unsaturated Disaccharides by Eliminative Cleavage of Heparin and Heparan Sulfate With Heparitinases", Comp. Biochem. Physiol., 103B: 473-479, 1992.
Lider et al. "Inhibition of T Lymphocyte Heparanase by Heparin Prevents T Cell Migration and T Cell-Mediated Immunity", European Journal of Immunology, 20: 493-499, 1990.
Lider et al. "Suppression of Experimental Autoimmune Diseases and Prolongation of Allograft Survival by Treatment of Animals With Low Doses of Heparins", The Journal of Clinical Investigation, 83: 752-756, 1989.
Neparstek et al. "Activated T Lymphocytes Produce A Matrix-Degrading Heparan Sulphate Endoglycosidase", Nature, 310: 241-244, 1984.
Psuja "Affinity of Binding of Radiolabeled (125 I) Heparin and Low Molecular Weight Heparin Fraction CY 222 to Endothelium in Culture", Folia Haematol., 114(3): 429-436, 1987.
Toivonen et al. "Rat Adjuvant Arthritis as A Model to Test Potential Antirheumatic Agents", Meth. and Find. Exptl. Clin. Pharmacol., 4(6): 359-363, 1982.
Asselot et al. "Heparin Fragments Regulate Collagen Phenotype and Fibronectin Synthesis in the Skin of Genetically Diabetic Mice", Biochemical Pharmacology, 38(6): 895-899, 1989.
Asselot-Chapel et al. "Biosyntheses of Interstitial Collagens and Fibronectin by Porcine Aorta Smooth Muscle Cells. Modulation by Low-Molecular-Weight Heparin Fragments", Biochimica et Biophysica Acta, 993: 240-244, 1989.
Rodén et al. "Heparin—An Introduction", Heparin and Related Polysaccharides, Plenum Press, p. 1-20, 1992.
Bezouška et al. "Oligosaccharide Ligands for NKR-P1 Protein Activate NK Cells and Cytotoxicity", Nature, 372: 150-157, 1994.
Müller et al. "Involvement of Chemokine Receptors in Breast Cancer Metastasis", Nature, 410: 50-56, 2001.

Sehgal et al. "Molecular Characterization of CXCR-4: A Potential Brain Tumor-Associated Gene", Journal of Surgical Oncology, 69: 239-248, 1998.

Sehgal et al. "CXCR-4, A Chemokine Receptor, Is Overexpressed in and Required for Proliferation of Glioblastoma Tumor Cells", Journal of Surgical Oncology, 69: 99-104, 1998.

Rossi et al. "The Biology of Chemokines and Receptors", Annu. Rev. Immunol., 18: 217-242, 2000.

Braun et al. "The CC Chemokine CKβ-11/MIP-3β/ELC/Exodus 3 Mediates Tumor Rejection of Murine Breast Cancer Cells Through NK Cells", The Journal of Immunology, 164: 4025-4031, 2000.

Bleul et al. "The Lymphocyte Chemoattractant SDF-1 Is A Ligand for LESTR/Fusin and Blocks HIV-1 Entry", Nature, 382: 829-833, 1996.

Riley et al "A Comparison of Sucralfate and Prednisolone Enemas in the Treatment of Active Distal Ulcerative Colitis", The Scandinavian Journal of Gastroenterology, 24(8): 1014-1018, 1989.

Basic & Clinical Immunology "Autoimmunity", Published by Lange Medical Publications in 1984, edited by Daniel P.Sites et al; chapter 12, pp. 152-186.

The Merck Manuel "The Merck Manuel of Diagnosis and Therapy", 17th Ed., p. 426-430, 872-875, 1999.

Venkataraman et al. "Sequencing Complex Polysaccharides", Science, 286: 537-542, 1999.

\* cited by examiner

Tables

Table 1.  Survival at day 49 after 3LL injection

| DS | live mice | dead mice | survival (%) * | p-value |
|---|---|---|---|---|
| DS Po912 | 11 | 5 | 68.75 | 0.0003 |
| DS Po821 | 7 | 9 | 43.75 | 0.014 |
| DS 1020 | 8 | 8 | 50 | 0.005 |
| DS 9267 | 7 | 9 | 43.75 | 0.014 |
| DS 9517 | 7 | 9 | 43.75 | 0.014 |
| DS 8892 | 4 | 12 | 25 | 0.14 |
| DS 8767 | 8 | 8 | 50 | 0.005 |
| DS 0895 | 7 | 9 | 43.75 | 0.014 |
| DS 1145 | 10 | 6 | 62.5 | 0.0008 |
| PBS (control) | 1 | 15 | 6.2 | |

* survival (%) = [live mice/total mice] x 100

Table 2. Weights of lungs at day 50 after 3LL injection

| Treatment with DS | Weights ± SD (gr.) | Decrease (%) * |
|---|---|---|
| DS Po912 | 0.37 ± 0.17 | 60.1 |
| DS Po821 | 0.28 ± 0.07 | 69.3 |
| DS 1020 | 0.28 ± 0.13 | 69.8 |
| DS 9267 | 0.51 ± 0.07 | 44.8 |
| DS 9517 | 0.43 ± 0.13 | 53.0 |
| DS 8892 | 0.66 ± 0.18 | 28.8 |
| DS 8767 | 0.44 ± 0.08 | 52.2 |
| DS 0895 | 0.49 ± 0.14 | 46.7 |
| DS 1145 | 0.59 ± 0.18 | 36.4 |
| PBS | 0.92 | |

* Decrease (%) = [1-(weights of treated group/weights of control group)] x 100

ANTI-CANCER THERAPEUTIC COMPOUNDS

CROSS-REFERENCE TO RELATED APPLICATIONS

This Application claims priority from U.S. patent application Ser. No. 09/495,723, filed on Feb. 1, 2000, which is a divisional of U.S. patent application Ser. No. 08/486,127, filed on Jun. 7, 1995 and now issued as U.S. Pat. No. 6,020,323, on Feb. 1, 2000, which is a continuation of U.S. patent application Ser. No. 08/436,330, filed on May 10, 1995, now U.S. Pat. No. 5,861,382, issued on Jan. 19, 1999, which claims priority from PCT Application No. PCT/US93/10868, filed on Nov. 9, 1993, and which is a continuation in part of U.S. patent application Ser. No. 08/096,739, filed on Jul. 23, 1993, abandoned, which is a continuation in part of U.S. patent application Ser. No. 07/974,750, filed on Nov. 10, 1992, abandoned, which is a continuation in part of U.S. patent application Ser. No. 07/878,188, filed on May 1, 1992, abandoned; all of which are owned in common with the present application, and all of which are hereby incorporated by reference as if fully set forth herein.

FIELD OF THE INVENTION

The present invention is of therapeutic compounds for cancer, and in particular, of therapeutic compounds which block the ability of cytokines and chemokines to promote metastasis of malignant cells, and which are heparin and heparan-sulfate derived saccharide compounds.

BACKGROUND OF THE INVENTION

Cancer and Metastasis

Cancer is a growing problem in the world, particularly in the western countries. The increase in cancer cases and in cancer-related mortality may be attributed, at least in part, to an overall decrease in the rate of deaths from other causes, such as infectious disease. Therefore, new treatments for cancer are becoming increasingly important, both in order to extend the lifespan and also to increase quality of life.

The mechanism basis of the ability of metastatic cells to home and proliferate in the parenchyma of certain organs, such as the liver, and to develop organ-specific metastases remain largely unknown. For metastasis to occur, the malignant cells must escape from the primary tumor, circulate through the blood stream and subsequently arrest and develop in the target tissues. Recently, it was shown that metastatic breast carcinomas utilize the SDF-1/CXCR4 chemokine/chemokine receptor pathway for metastasis (1-3).

In recent years, chemokines, molecules that actively modulate the onset and progression of the immune response, and their cellular receptors have received increasing attention due to their critical role in the progression of immune disease states such as Asthma, Atherosclerosis, Graft Rejection, AIDS, and Multiple Sclerosis (MS). Chemokines are a family of structurally related proteins that have an essential role in the recruitment and activation of cells from the immune system. Thus, chemokines can be considered as master regulators of the body's immune response repertoire. Because of their varied activities, chemokines are potentially valuable targets for therapeutic intervention in a wide range of diseases (4).

Several research groups have shown anti-tumor activity with a variety of chemokines overexpressed in tumor cells. More specifically, anti tumor activity was shown for MCP-3, MIP-1alpha, Rantes, lymphotactin, TCA-3, and MIP-3alpha (5). The chemokine receptor CXCR-4 has been shown to function as the major co-receptor for HIV-1/2 on T cells, as well as the CD4-independent receptor for HIV-2 (6). The murine CXCR-4-predicted amino acid sequence is 91% identical to human CXCR-4. CXCR-4 is expressed on human CD34+ stem cells, PBLs, monocytes, and neutrophils (7). Stromal cell-derived factor 1 alpha/beta (SDF-1), the ligand for CXCR-4, is a powerful chemoattractant for T cells and CD34+ cells and can inhibit HIV infection of these cells (8). Human and murine SDF-1 differ by one amino acid and are cross-reactive. SDF-1 is produced in high levels in the bone marrow, lymph node (LN) and spleen (9-11). In contrast to pro-inflammatory chemokines, SDF-1 expression is not regulated by stimuli generated by viral or bacterial infections, suggesting a major role for SDF-1 in steady-state homeostatic processes, such as leukocyte trafficking (12).

SDF-1 can induce the arrest of rolling $CD34^+$ on human endothelium under shear flow in vitro, and that in vivo, human bone marrow endothelial cells express SDF-1 (13). Furthermore, by increasing the expression level of CXCR4 on CD34+ progenitors, their ability to migrate to and engraft in the bone marrow is improved (14). Overexpression of human CXCR4 on murine T cells led to enhanced numbers of these cells in the murine BM and to a dramatic decrease in their numbers in the circulation (15). In addition, injection of SDF-1 into the murine spleen and bone marrow was shown to increase the homing of FDCP-mix cells to the spleen and the homing of human CD34+ cells to the bone marrow (16). These results suggest that an increase in the concentration of SDF-1 within the bone marrow microenvironment or enhanced expression of CXCR4 on effector T cells may stimulate the homing and retention of these cells to the bone marrow.

The process of metastasis requires at least three consecutive steps in which chemokines may be involved. First, chemokines may facilitate the interaction of tumor cells with endothelial cells. Second, following the transendothelial migration of tumor cells chemokines can direct the intra-tissue localization of tumors. Thereafter chemokines may stimulate the growth of tumor cells after metastasis.

Saccharide-based Compounds

Heparin is a glycosaminoglycan, a polyanionic sulfated polysaccharide, which is used clinically to prevent blood clotting as an antithrombotic agent. In animal models, heparin has been shown to reduce the ability of autoimmune T lymphocytes to reach their target organ (Lider, O. et al., Eur. J. Immunol. (1990) 20:493-499). Heparin was also shown to suppress experimental autoimmune diseases in rats and to prolong the allograft survival in a model of skin transplantation in mice, when used in low doses (5.mu.g for mice and 20.mu.g for rats) injected once a day (Lider, O. et al., J. Clin. Invest. (1989) 83:752-756).

The mechanisms behind the observed effects are thought to involve inhibition-of release by T lymphocytes of enzyme(s) necessary for penetration of the vessel wall, primarily the enzyme heparanase that specifically attacks the glycosaminoglycan moiety of the sub-endothelial extracellular matrix (ECM) that lines blood vessels (Naparstek, Y. et al., Nature (1984) 310:241-243). Expression of the heparanase enzyme is associated with the ability of autoimmune T lymphocytes to penetrate blood vessel walls and to attack the brain in the model disease experimental autoimmune encephalomyelitis (EAE).

European Patent Application EP 0114589 (Folkman et al.) describes a composition for inhibition of angiogenesis in mammals in which the active agents consist essentially of (1) heparin or a heparin fragment which is a hexasaccharide or larger and (2) cortisone or hydrocortisone or the 11-.alpha. isomer of hydrocortisone. According to the disclosure, heparin by itself or cortisone by itself are ineffective; only the combination of both gives the desired effects. Although there is no proof in the literature that there is a connection between angiogenesis and autoimmune diseases, the description on page 5 of the patent application connects angiogenesis with psoriasis and with arthritis, indicating the use of high doses of 25,000 units to 47,000 units of heparin per day (i.e., about 160 to about 310 mg per day).

Horvath, J. E. et al., in Aust. N.Z.J. Med. (1975) 5(6): 537-539, describe the effect of subanticoagulant doses of subcutaneous heparin on early renal allograft function. The daily dosage is high (5000 U or about 33 mg) and the conclusion of the study is that heparin in subanticoagulant doses has no effect on early graft function or graft survival and that it may be associated with increased hemorrhagic complications.

Toivanen, M. L. et al., Meth. and Find. Exp. Clint. Pharmacol. (1982) 4(6):359-363, examined the effect of heparin in high dosage (1000 U/rat or about 7 mg/rat) in the inhibition of adjuvant arthritis in rats and found that heparin enhanced the severity of the rat adjuvant arthritis.

PCT Patent: Application PCT/AU88/00017 published under No. WO88/05301 (Parish et al.) describes sulphated polysaccharides that block or inhibit endoglycosylase activity, such as heparanase activity, for use as antimetastatic and anti-inflammatory agents. Heparin and heparin derivatives, such as periodate oxidized, reduced heparins, that had negligible anticoagulant activity, were shown to have anti-metastatic and anti-inflammatory activity when used in dosages within, the range of 1.6-6.6 mg per rat daily, administered by constant infusion (corresponding to 75-308 mg daily for an adult human patient).

Heparin and heparan sulfate are closely related glycosaminoglycan macromolecules. The degradation products of these polymeric macromolecules, which are termed low molecular weight heparins (LMWH), may have the same or greater pharmacological effects on the blood clotting system as the parent macromolecules. Furthermore, because there is extensive but incomplete post-synthetic processing of the polymer's basic disaccharide subunit, glucuronic acid and N-acetyl glucosamine, the LMWH will be a heterogeneous mixture not only of sizes but also of chemical compositions (See Goodman and Gilman's The Pharmacological Basis of Therapeutics, 8th Ed., (Pergamon Press, New York, 1990) pp. 1313-1315. Methods to obtain low molecular weight products from heparin, which are useful as anticoagulants, are described in the art. These methods seek to optimize the persistence in vivo or the extent of hemorrhagic side effects of their products (See, for example, Alpinro R. R., et al., U.S. Pat. No. 5,010,063; Choay, J., et al., U.S. Pat. No. 4,990,502; Lopez, L. L., et al., U.S. Pat. No. 4,981,955). Others teach the use of affinity chromatographic methods to obtain low molecular weight products (See, for example, Rosenberg, R. D., et al., U.S. Pat. No. 4,539,398 and Jordan, R. E., et al., U.S. Pat. No. 4,446,314).

Psuja, P., as reported in Folio Haematol. (Leipz), (1987) 114:429-436, studied the effect of the heterogeneity of heparins on their interactions with cell surfaces. Psuja reported that there are moderate affinity receptors for LMWH found on cultured endothelial cells, but he-determined that the upper limit of the fraction of LMWH bound to these receptors was less than 1% of total LMWH.

Other workers have demonstrated effects of LMWH on the metabolism of a variety of cultured cell types. Asselot-Chapel, C., et al., in Biochem. Pharmacol. (1989) 38:895-899 and Biochem. Biophys. Acta, (1989) 993:240-244, report that LMWH cause cultured smooth muscle cells to decrease the ratio of type III to type I collagen and fibronectin synthesis. Rappaport, R. in U.S. Pat. No. 4,889,808, teaches that LMWH can cause human diploid pulmonary fibroblasts, cultured in the absence of serum, to respond to LMWH by increased secretion of tissue plasminogen activator and related proteins.

Effects of LMWH on complex multicellular systems have been reported, for example in Folkman et al. and Lider et al., in EPO Application 0114589 and J. Clin. Invest. (1989) 83:752:756. In addition, Diferrante, N., in published International Application WO 90/03791, teaches the use of LMWH to inhibit the reproduction of HIV in cultures of C8166 transformed human lymphocytes (ALL). However, none of the prior art experiments that have studied the effects of LMWH on cellular metabolism has considered that the heterogeneity of LMWH may produce antagonistic effects. Furthermore, none has shown or suggested a regulatory effect on cytokine activity based on the use of substantially pure oligosaccharide substances.

Cahalon et al. (International Immunology, vol. 9, p, 1517-1522, 1997; see also Lider et al., Proc. Natl. Acad. Sci. USA, vol 92, p. 5037-5041, 1995) describe the ability of heparin disaccharides to inhibit tumor necrosis factor alpha production by macrophages. These disaccharides are also able to stop the immunologically based inflammation process in rodents. Also, disaccharides derived from heparin or heparan sulfate were shown to block IL-8 and IL-1β secretion by intestinal epithelial cells (Chowers et al., Gastroenterology, vol 120, p. 449-459, 2001) and to modulate chemokine-induced T-cell adhesion to the extracellular matrix (Hershkoviz et al., Immunology, vol 99, p. 87-93, 2000).

SUMMARY OF THE INVENTION

The background art does not teach or suggest the use of LMWH, or substances derived from such compounds, for the treatment of cancer. In particular, the background art does not teach or suggest the use of such compounds for prevention of metastasis and/or for the prevention of induction of cell migration. Furthermore, the background art does not teach or suggest the use of glucosamine derivatives for treatment of cancer, and/or prevention of metastasis and/or for the prevention of induction of cell migration. In particular, the teachings of the background art with regard to the inhibition of T-cell adhesion do not teach or suggest any efficacy against malignancies, or against the migration of malignant cells.

The present invention is of therapeutic compounds for treatment of cancer, and in particular, of therapeutic compounds which block the ability of cytokines and chemokines to promote metastasis of malignant cells. The therapeutic compound comprises a carboxylated and/or sulfated oligosaccharide, preferably in a substantially purified form, which is a heparin or heparan-sulfate derived saccharide compound. In one embodiment of the present invention, the carbohydrate or oligosaccharide has a molecular weight of no more than about 3000 daltons, preferably lying in the range of about 400 to about 2000 daltons, most preferably between about 400 and about 1100 daltons. Generally, substances of the present invention which inhibit tumor cell migration, as determined by biological assays (described more fully, below), comprise molecules of various sugar units of which the basic unit of activity is associated with a disaccharide. However, larger oligosaccharide chains of up to about 10 sugar units, containing the basic disaccharide unit of activity can also function to inhibit such activity.

The substances of the present invention may be obtained from natural sources, including living organisms. For example, active substances have been isolated and purified from low molecular weight heparin (LMWH) fractions, as well as extracellular matrices that have been degraded by the action of an enzyme, e.g., heparanase derived from animals (mammals) or microorganisms (bacteria). Yet another source of active substances is enzyme-treated heparin (e.g., endoglycosylase-degraded heparin).

A preferred class of oligosaccharides is the glucosamine derivatives, particularly those derivatives which are sulfated. More preferably, the oligosaccharides are N-sulfated 4-deoxy-4-en-iduronoglucosamine having at least one other sulfate group, or an N-acetylated 4-deoxy-4-en-iduronoglucosamine having at least two sulfate groups, as well as pharmaceutically acceptable salts thereof. Most preferably, the oligosaccharides are disaccharides of formula (I) or its pharmaceutically acceptable salt:

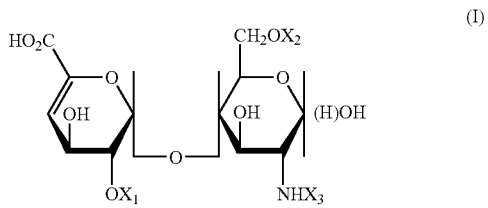

(I)

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates.

Non-limiting examples of preferred saccharide compounds for use in the present invention are given in the table below. The reference "Sigma (number)" refers to the product number for this compound, which may be ordered from Sigma Chemicals (USA). The reference "CAS number (number)" refers to the CAS index number for these compounds, according to which the compound may be obtained from a chemical supplier. Please note that the structures of these compounds are given below, in an Appendix.

| List of Heparin and Heparan sulfate Disaccharides |
| --- |
| Po912 |
| Sigma H 9392, |
| (α-ΔUA-2S-[1→4]-GlcNS), |
| produced by the action of |
| heparinase I and II on heparin, CAS |
| number 136098-03-8. |
| Po821 |
| A novel DS, Synthetic, |
| (GlcNS,6S-[1→4]-GlcA-2S), |
| produced by the action of heparanase on |
| heparan sulfate. |
| DS 1020 |
| Sigma H 1020, |
| (α-ΔUA-[1→4]-GlcNS-6S), |

| List of Heparin and Heparan sulfate Disaccharides |
| --- |
| produced by the action of heparinase II |
| on heparin. |
| DS 9267 |
| Sigma H 9267, |
| (α-ΔUA-2S-[1→4]-GlcNS-6S), |
| produced by the action of heparinase I |
| and II on heparin, CAS number 136098-10-7. |
| DS 9517 |
| Sigma H 9517, |
| (α-ΔUA-2S-[1→4]-GlcNAc-6S), |
| produced by the action of heparinase II |
| on heparin. |
| DS 8892 |
| Sigma H 8892, |
| (α-ΔUA-2S-[1→4]-GlcN-6S), |
| produced by the action of heparinase on |
| heparin. |
| DS 8767 |
| Sigma H 8767, |
| (α-ΔUA-2S-[1→4]-GlcNAc), |
| produced by the action of heparinase II |
| on heparin. |
| DS 0895 |
| Sigma H 0895, |
| (α-ΔUA-[1→4]-GlcNAc), |
| produced by the action of heparinase II |
| and III on heparin. |
| DS 1145 |
| Sigma H 1145, |
| (α-ΔUA-[1→4]-GlcNS), |
| produced by the action of heparinase II |
| and III on heparin. |

Abbreviation:
ΔUA = 4-deoxy-$_L$-threohex-4-enopyranosyluronic acid.
GlcA = β-D-glucopyranoside uronic acid.
GlcN = D-glucosamine.
Ac = Acetyl.
NS, 2S, 6S, = N-sulfo, 2-sulfate and 6-sulfate respectively.

Hereinafter, the term "substantially purified form" means that specific steps have been taken to remove non-active components, or components that have an opposing effect, from the oligosaccharide substances and to isolate the active moiety or moieties from mixtures or supernatants, such as those obtained from enzymatic degradation. Specifically, the substances claimed in the present invention are obtained from a rigorous chromatographic process, in which low-pressure size-exclusion gel chromatography (i.e., chromatography on Sephadex columns) is but an initial step in the purification scheme. Subsequent to the low-pressure separation, high-pressure liquid chromatographic (HPLC) techniques are used to isolate individual component oligosaccharides. Preferably, these steps have resulted in the purification of the individual active substances to substantial homogeneity.

Such a preferred purification step may include, for example, passing mixtures containing the active substance (e.g., fractions obtained from low pressure gel chromatography) through gel permeation HPLC or strong anion exchange (SAX) HPLC columns. Thus, substances comprising oligosaccharides selected from the group consisting of di-, tri-, tetra-, penta-, or hexasaccharides, preferably disaccharides, have been observed and isolated. The oligosaccharides of the present invention are carboxylated and/or sulfated and are, therefore, negatively charged. Particular embodiments of the invention preferentially include disaccharides having three negatively charged groups. Those that exhibit a specific inhibitory activity possess a molecular weight ranging from about 400 to about 2000, preferably, about 400 to about 1100.

When purified these substances or the compositions that contain them are substantially free of other substances that exert the opposite or antagonistic effect. Thus, a substance exhibiting inhibitory activity ("down" regulation) in a substantially purified form would be substantially free not only of other substances, in general, but of other substances that exhibit augmentation or retard the inhibitory activity of the "down" regulator. The situation would, of course, be reversed in the case of an augmentative substance (i.e., "up" regulators), in which the substance would be substantially free of other substances, particularly those that "down" regulate or antagonize augmentation.

The phrase "regulatory effect" includes both the up regulation or down regulation of any process affecting the availability or resulting activity in vivo or in vitro of cytokines which are generally functional to promote or otherwise support migration of malignant cells, including but not limited to, the cytokines IL-1, IL-6, and TNF-alpha and the chemokines IL-8, SDF-1, IP_10, MIG, I-TAC etc. Thus, compositions of the present invention may exert a regulatory effect on the host production of such a cytokine, on the host secretion of such a cytokine, on the extracellular availability of such a cytokine, or on the active forms of such a cytokine in a host. For instance, but not wishing to be limited by theory, the instant invention may act to elicit the secretion of a substance, such as a protein, which may bind to such a cytokine, change its conformation, and, consequently, affect its biological activity. It is also possible that the compositions of the present invention may, in penetrating a malignant cell, bind to particular oligonucleotide sequences and, thus, affect transcriptional or translational processes that ultimately alter protein synthesis. The compositions may also work through binding to cell surface receptors.

To simplify the following discussion, reference will be made, among others, to the "secretion of active cytokine" or the regulation of the "activity of a cytokine" with the understanding that a much broader meaning is to be attached to these phrases which encompasses the actual mechanism that is responsible for or the actual manner by which the observed augmentation or inhibition of the cytokine activity is effected by the substances and compositions of the present invention.

Hereinafter, the term "biologically active" refers to molecules, or complexes thereof, which are capable of exerting an effect in a biological system.

BRIEF DESCRIPTION OF THE DRAWINGS AND TABLES

The invention is herein described, by way of example only, with reference to the accompanying drawings and tables, wherein:

FIG. 1 shows the inhibition of migration of human T cells by DS II (9267);

FIG. 2 demonstrates that immobilized SDF-1 stimulates T cell adhesion to VCAM-1, which in turn is inhibited by DS 9267;

Figure 1:
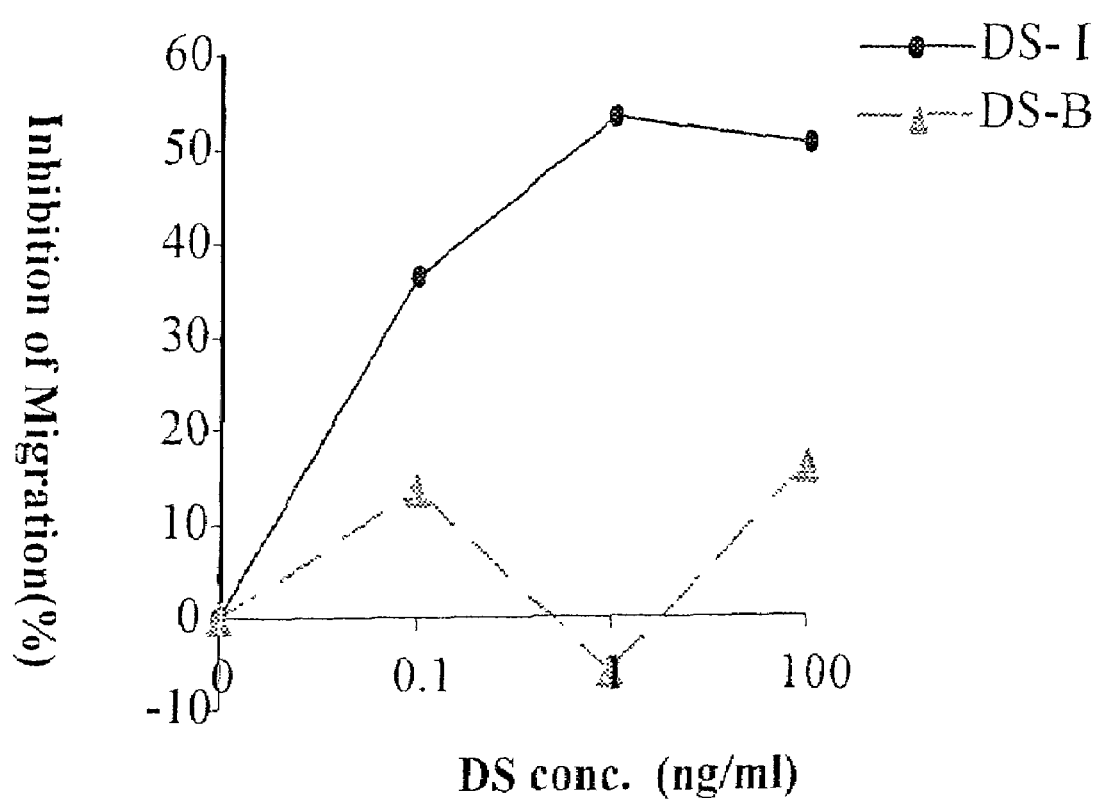

Table 1 shows survival of mice at day 49 after injection with the tumor cells; and Table 2 shows weights of lungs of the mice at day 50 after injection with the tumor cells.

DESCRIPTION OF THE PREFERRED EMBODIMENTS

The present invention is of therapeutic compounds for the treatment of cancer, and in particular, of therapeutic compounds which block the ability of cytokines and chemokines to promote metastasis of malignant cells. The therapeutic compound comprises a carboxylated and/or sulfated oligosaccharide, preferably in a substantially purified form, which is a heparin or heparan-sulfate derived saccharide compound. Hereinafter, the term "heparin or heparan-sulfate derived" refers to any oligosaccharide obtained from, or otherwise structurally homologous to, any portion of heparin or heparan-sulfate.

In one embodiment of the present invention, the carbohydrate or oligosaccharide has a molecular weight of no more than about 3000 daltons, preferably lying in the range of about 400 to about 2000 daltons, most preferably between about 400 and about 1100 daltons. Generally, substances of the present invention which inhibit tumor cell migration, as determined by biological assays (described more fully, below), comprise molecules of various sugar units of which the basic unit of activity is associated with a disaccharide. However, larger oligosaccharide chains of up to about 10 sugar units, containing the basic disaccharide unit of activity can also function to inhibit such activity.

A preferred class of oligosaccharides is the glucosamine derivatives, particularly those derivatives which are sulfated. More preferably, the oligosaccharides are N-sulfated 4-deoxy-4-en-iduronoglucosamine having at least one other sulfate group, or an N-acetylated 4-deoxy-4-en-iduronoglucosamine having at least two sulfate groups, as well as pharmaceutically acceptable salts thereof. Alternatively and more preferably, the oligosaccharides are N-sulfated or N-acetylated 4-deoxy-4-en-glucuronoglucosamine or a pharmaceutically acceptable salt thereof. Such compounds, if N-sulfated, have at least one other sulfate group and, if N-acetylated, have at least two sulfate groups.

Most preferably, the oligosaccharides are disaccharides of formula (I) or its pharmaceutically acceptable salt:

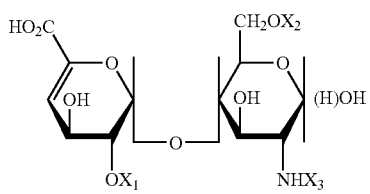

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates.

Illustrative but non-limiting examples of such compounds are disclosed in the previously incorporated patents/applications, which were incorporated by reference above.

The present invention also discloses methods for treating malignancies. Hereinafter, the term "treatment" includes both the prevention of the genesis of the malignancy, as well as the substantial reduction or elimination of malignant cells and/or symptoms associated with the development and metastasis of malignancies. Malignancies for which the therapeutic agents of the present invention are useful include all metastatic tumors. Examples of tumors for which such a treatment would be effective include, but are not limited to, breast cancers such as infiltrating duct carcinoma of the breast or other metastatic breast cancers, lung cancers such as small cell lung carcinoma, bone cancers, bladder cancers such as bladder carcinoma, rhabdomyosarcoma, angiosarcoma, adenocarcinoma of the colon, prostate or pancreas, or other metastatic prostate or colon cancers, squamous cell carcinoma of the cervix, ovarian cancer, malignant fibrous histiocytoma, skin cancers such as malignant melanoma, lymphomas and leukemia, leiomyosarcoma, astrocytoma, glioma and heptocellular carcinoma.

Such treatment may optionally and preferably be performed by systemic administration of the therapeutic compound according to the present invention. A preferred route of administration is oral, but alternative routes of administration include, but are not limited to, intranasal, intraocular, sub-cutaneous and parenteral administration. Such treatment may be performed topically, for example for skin malignancies, including but not limited to, metastatic melanoma. Other routes of administration, and suitable pharmaceutical formulations thereof, are described in greater detail below.

The following description is divided into sections for ease of discussion only and without any intention of being limiting. Section 1 describes illustrative and preferred compounds according to the present invention. Section 2 describes tests performed to demonstrate the efficacy of these compounds. Section 3 describes exemplary formulations and methods of use of these compounds for treatment of malignancies.

Section 1: Illustrative Saccharide Compounds

The present invention encompasses a number of preferred saccharide compounds. The therapeutic compound comprises a carboxylated and/or sulfated oligosaccharide, preferably in a substantially purified form, which is a heparin or heparan-sulfate derived saccharide compound. In one embodiment of the present invention, the carbohydrate or oligosaccharide has a molecular weight of no more than about 3000 daltons, preferably lying in the range of about 400 to about 2000 daltons, most preferably between about 400 and about 1100 daltons. Generally, substances of the present invention which inhibit tumor cell migration, as determined by biological assays (described more fully, below), comprise molecules of various sugar units of which the basic unit of activity is associated with a disaccharide. However, larger oligosaccharide chains of up to about 10 sugar units, containing the basic disaccharide unit of activity can also function to inhibit such activity.

The substances of the present invention may be obtained from natural sources, including living organisms. For example, active substances have been isolated and purified from low molecular weight heparin (LMWH) fractions, as well as extracellular matrices that have been degraded by the action of an enzyme, e.g., heparanase derived from animals (mammals) or microorganisms (bacteria). Yet another source of active substances is enzyme-treated heparin (e.g., endoglycosylase-degraded heparin).

Non-limiting examples of tested saccharide compounds are given in the table below. The reference "Sigma (number)" refers to the product number for this compound, which may be ordered from Sigma Chemicals (USA). The reference "CAS number (number)" refers to the CAS index number for these compounds, according to which the compound may be obtained from a chemical supplier. Please note that the structures of these compounds are given at the end, in an Appendix.

| List of Heparin and Heparan sulfate Disaccharides |
| --- |
| Po912 |
| Sigma H 9392, |
| (α-ΔUA-2S-[1→4]-GlcNS), |
| produced by the action of |
| heparinase I and II on heparin, CAS |
| number 136098-03-8. |
| Po821 |
| A novel DS, Synthetic, |
| (GlcNS,6S-[1→4]-GlcA-2S), |
| produced by the action of heparanase on |
| heparan sulfate. |
| DS 1020 |
| Sigma H 1020, |
| (α-ΔUA-[1→4]-GlcNS-6S), |
| produced by the action of heparinase II |
| on heparin. |
| DS 9267 |
| Sigma H 9267, |
| (α-ΔUA-2S-[1→4]-GlcNS-6S), |
| produced by the action of heparinase I |
| and II on heparin, CAS number 136098-10-7. |
| DS 9517 |
| Sigma H 9517, |
| (α-ΔUA-2S-[1→4]-GlcNAc-6S), |
| produced by the action of heparinase II |
| on heparin. |
| DS 8892 |
| Sigma H 8892, |
| (α-ΔUA-2S-[1→4]-GlcN-6S), |
| produced by the action of heparanase on |
| heparin. |
| DS 8767 |
| Sigma H 8767, |
| (α-ΔUA-2S-[1→4]-GlcNAc), |
| produced by the action of heparinase II |
| on heparin. |
| DS 0895 |
| Sigma H 0895, |
| (α-ΔUA-[1→4]-GlcNAc), |
| produced by the action of heparinase II |
| and III on heparin. |

-continued

List of Heparin and Heparan sulfate Disaccharides

DS 1145
Sigma H 1145,
(α-ΔUA-[1→4]-GlcNS),
produced by the action of heparinase II
and III on heparin.

Abbreviation:
ΔUA = 4-deoxy-L-threohex-4-enopyranosyluronic acid.
GlcA = β-D-glucopyranoside uronic acid.
GlcN = D-glucosamine.
Ac = Acetyl.
NS, 2S, 6S, N-sulfo, 2-sulfate and 6-sulfate respectively.

EXAMPLE 1

Testing of Compounds In vitro

Compounds according to the present invention, as described in the table given above, were tested in vitro for their ability to block the migration of cells in response to the chemokine SDF-1. The experiments are described in greater detail below.

Materials and Methods

Human T cells were pretreated with DS II (9267) or DS-B (control DS 8767) (100 ng/ml, 30 min), both obtained from Sigma-Aldrich Chemicals (USA). The cells were then placed on FN-coated membranes in the upper wells of a chemotaxis chamber that contained SDF-1alpha (250 ng/ml) in the lower compartment. Migrating cells were collected from the lower wells after 1.5 hr (see FIG. 1 for results).

Figure 2:
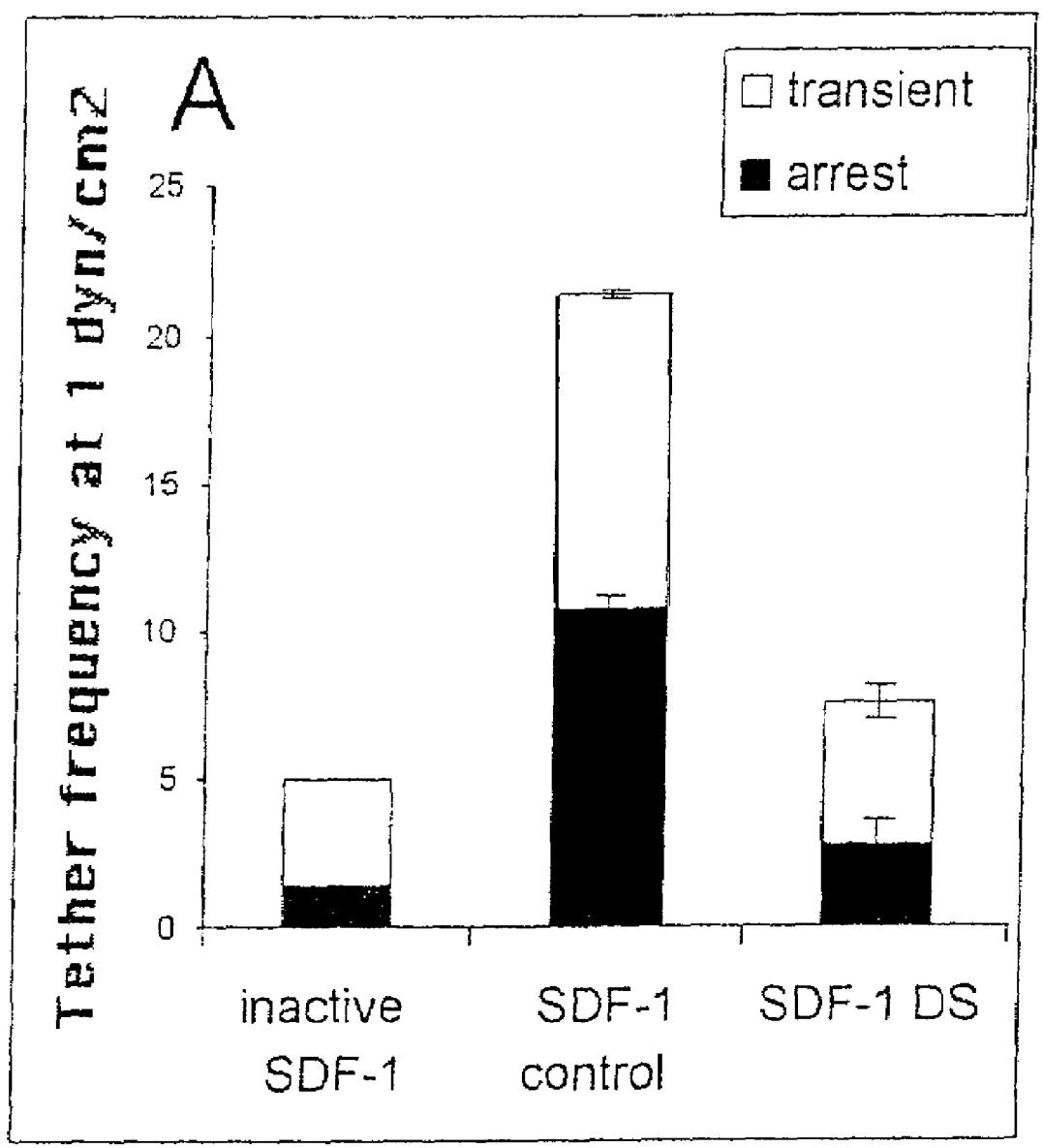

The effect of immobilized SDF-1 or inactive SDF-1 (co-coated at 2µg/ml with sVCAM-1 as explained in Materials and Methods) on the accumulation of T cells before and after treatment with DS 9267 was examined (see FIG. 2 for results).

The effect of disaccharide compounds according to the present invention on SDF-1alpha induced $Ca^{++}$ mobilization in RBL-2H3 cells was examined. Flue-3 labeledRBL-2H3 cells were treated with SDF-1α in the presence or absence of DS-II pretreatment, and $Ca^{2+}$ influx was measured (see FIG. 3).

Serum-starved PBLs were stimulated with either SDF-1α alone (250 ng/ml) or together with DS-9267 (100 ng/ml). Cell lysates were then resolved on SDS-PAGE gels, transferred to a nitrocellulose membrane and blotted with antibodies raised aginst ERK1/2, phospho-ERK1/2, Pyk-2 and phospho Pyk-2. Densitometric analysis is presented (see FIG. 4).

Chemokine and chemotaxis assays were performed as follows. Chemotaxis experiments were assayed by using Costar (Cambridge, Mass., 6.5 mm/diameter, 5 µm/pore) transwell plates. 100 µl chemotaxis buffer (RPMI 1640, 1% FCS) containing $2 \times 10^5$ T cells+ were added to the upper chamber, and 0.6 ml of chemotaxis buffer with or without SDF-1alpha was added to the bottom chamber. After 4 hours, migrating (bottom chamber) and non migrating (upper chamber) cells were counted for 30 seconds using a FACSort (B.D).

Laminar flow adhesion assays were performed as follows. Soluble VCAM-1 adhesion molecule was diluted at indicated concentrations in coating medium (PBS buffered with 20 mM bicarbonate pH 8.5) and adsorbed as 20 microliter spots on polystyrene plates (a polystyrene 60×15 mm petri dish, Becton Dickinson, Lincoln Park, N.J.) either for 2 hr at 37° C. sVCAM-1 was coated at 1-10 microgram/ml in the presence of 2 microgram/ml HSA carrier. The plates were then washed three times with PBS and blocked with HSA (20 mg/ml in PBS) for 2 hrs at room temperature. To co-coat the adhesive spots with SDF-1, washed plates were coated with 10 microgram/ml SDF-1 in PBS for 30 min at room temperature, before being blocked with HSA. The accumulation of T cells before and after treatment with DS 9267 was examined (see FIG. 2 for results).

Results

Figure 3:
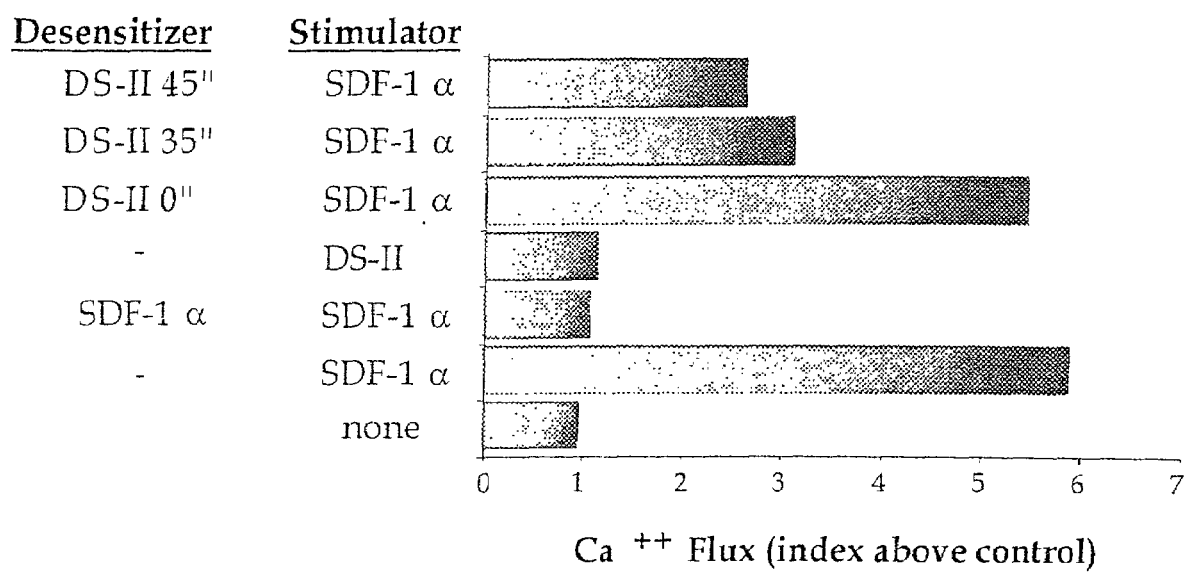
FIG. 3 shows that DS-II (9267) inhibits SDF-1alpha induced $Ca^{++}$ mobilization in RBL-2H3 cells.

Disaccharide (DS) molecules were found to inhibit T cell migration in response to the chemokine SDF-1α (FIG. 1). Furthermore, these molecules were able to block the chemokine-mediated interaction of cells with endothelial ligands such as VCAM-1 (FIG. 2). The same molecules inhibit SDF-1alpha induced $Ca^{++}$ mobilization in the mast cell leukemia RBL-2H3 cells (FIG. 3).

Figure 4:
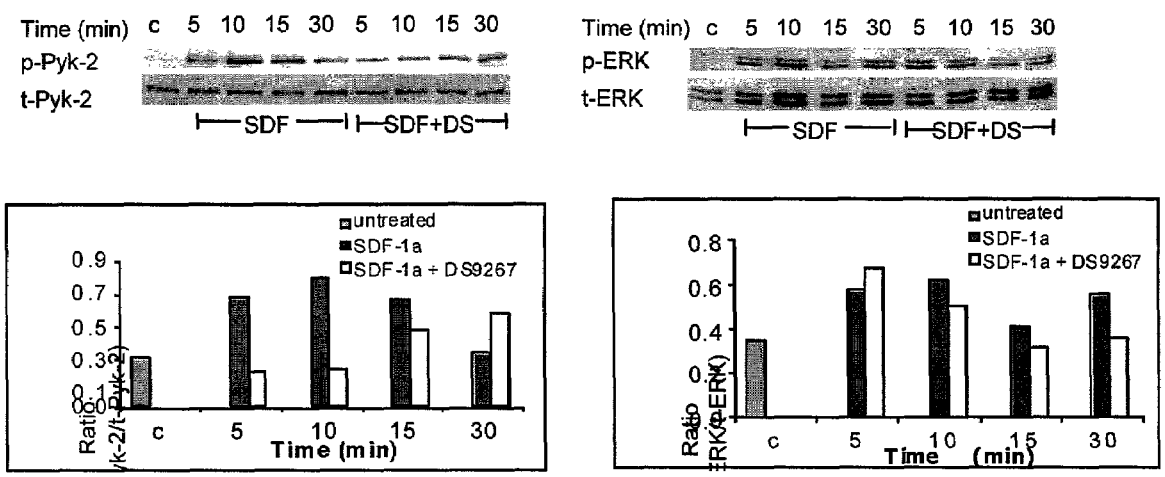
FIG. 4 shows that co-stimulation of PBLs with SDF-1alpha and DS-9267 results in down-regulation of Pyk-2 and ERK1/2 phosphorylation.

Without wishing to be limited to a single hypothesis, these results support the possibility that disaccharides, such as those which may optionally be produced by the enzymatic degradation of HS or heparin, exert their activity by interfering with the CXCR4 7TM-GPCR signaling pathway. This hypothesis was therefore examined by studying the phosphorylation and activation of Pyk-2 and ERK1/2. Co-stimulation of PBLs with SDF-1alpha and DS results in down-regulation of Pyk-2 and ERK1/2 phosphorylation (FIG. 4). $Ca^{++}$ mobilization and phosphorylation of Pyk-2 and ERK1/2 are key regulatory events that regulate cell migration and proliferation of tumor cells. Thus, these additional results further support the possibility that disaccharides according to the present invention exert their anti-migratory effect at least partially by interfering with the CXCR4 7TM-GPCR signaling pathway.

Regardless of the exact pathway or pathways through which the effect is exerted, the above results demonstrate that the saccharide compounds of the present invention are able to block migration of cells.

EXAMPLE 2

Testing of Compounds In vivo

Compounds according to the present invention, as described in the table given above, were tested in vivo. Briefly, mice were inoculated with tumor cells obtained from lung carcinoma. The mice were then treated with the compounds according to the present invention. Treatment with the different disaccharides, except for DS8892, resulted in a significant increase in the survival rate of the mice. Treatment with DS Po912 and DS 1145 appeared to provide the best treatment, at least in terms of inhibition of mortality.

Materials and Methods

Disaccharide Compounds

The disaccharide compounds were obtained from Sigma-Aldrich Chemicals (USA), with the exception of Po821, which was prepared by the inventors as previously described, in the patents/applications which were incorporated by reference (see for example U.S. Pat. Nos. 5,861,382 and 6,020,323; all of which were previously incorporated by reference).

Chemokine and chemotaxis assays were performed as follows. Chemotaxis experiments were assayed by using Costar (Cambridge, Mass., 6.5 mm/diameter, 5 µm/pore) transwell plates. 100 µl chemotaxis buffer (RPMI 1640, 1% FCS) containing $2 \times 10^5$ T cells+ were added to the upper chamber, and 0.6 ml of chemotaxis buffer with or without SDF-1 was added to the bottom chamber. After 4 hours, migrating (bottom chamber) and non migrating (upper chamber) cells were counted for 30 seconds using a FACSort (B.D).

Experimental Animals

C57BL/6, 12 months old male mice were obtained from the Jackson Laboratory.

Cells

Syngeneic, 3LL lewis lung carcinoma, variant D122, was obtained from the Weizmann Institute of Science. This tumor line develops metastases in the lungs after intravenous (iv) inoculation.

Cells were cultured in DMEM medium containing high glucose and supplemented with 10% FCS, glutamine and penicillin.

Tumor Cell Inoculation

Cells were incubated 24 hr before inoculation into the mice with the different disaccharides (300 ng/ml) in culture medium. Then, the cells were washed and injected i. v., (500,000 cells per mouse) in 100 μl PBS containing 30 ng of the corresponding disaccharide.

The number of dead mice was counted each day after the inoculation was performed. The mice were sacrificed at day 50 and the weights of their lung were determined.

Disaccharide Treatment

Each group, injected by one of the disaccharides, contained 16 mice. Control mice received PBS alone. The different disaccharides, were injected to the mice subcutaneously (30 ng per mouse in 0.1 ml of PBS), one day before and one and two days after cell inoculation.

Results

Figure 5:
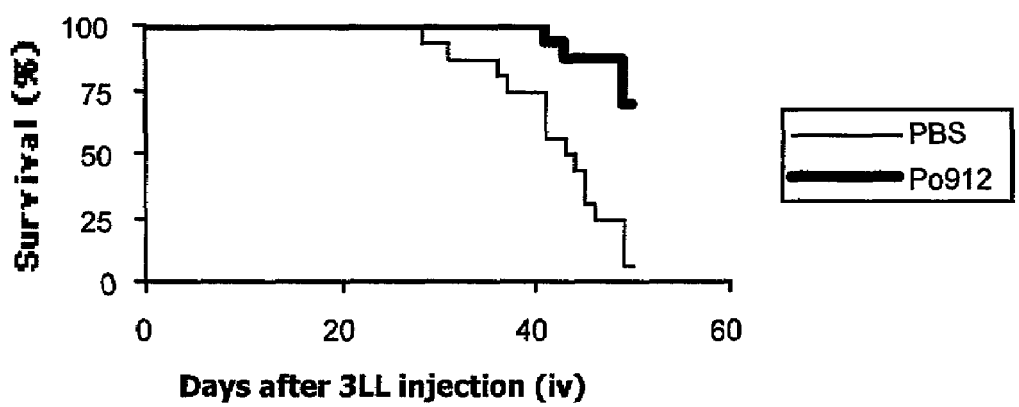
FIG. 5 is a graph showing the effect of treatment of mice with DS Po912.
Figure 6:
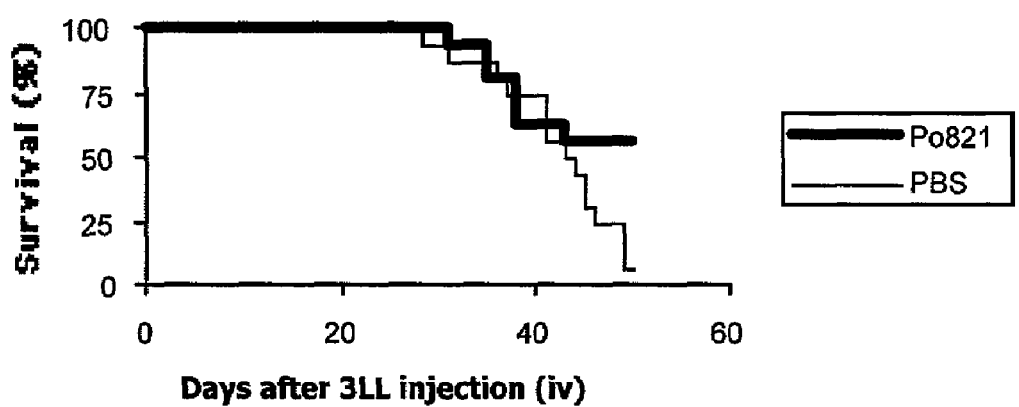
FIG. 6 is a graph showing the effect of treatment of mice with DS Po821.
Figure 7:
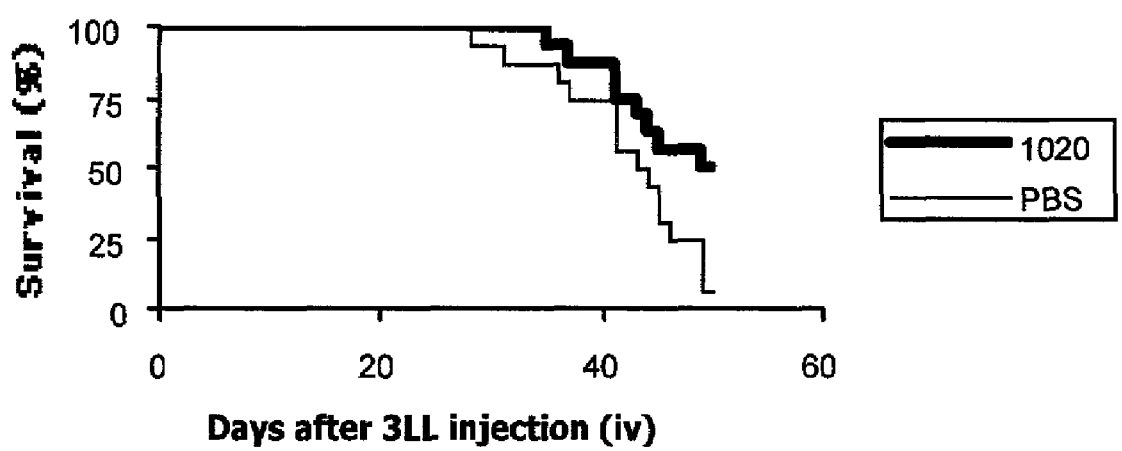
FIG. 7 is a graph showing the effect of treatment of mice with DS 1020.
Figure 8:
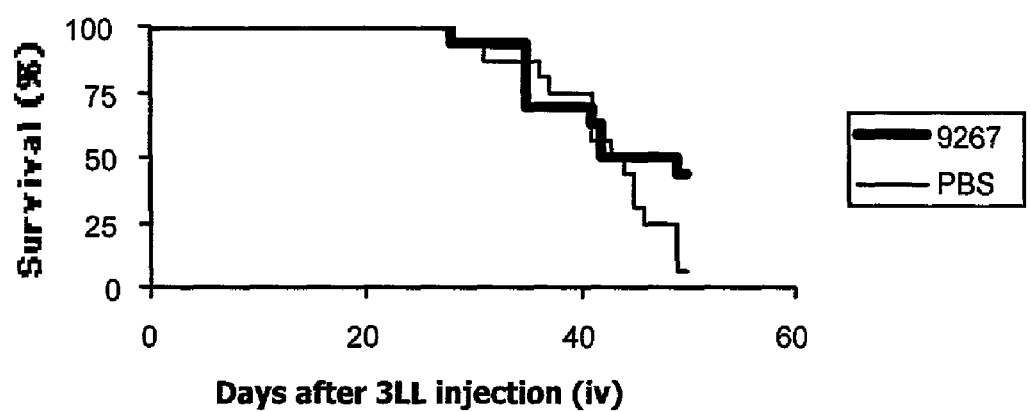
FIG. 8 is a graph showing the effect of treatment of mice with DS 9267.
Figure 9:
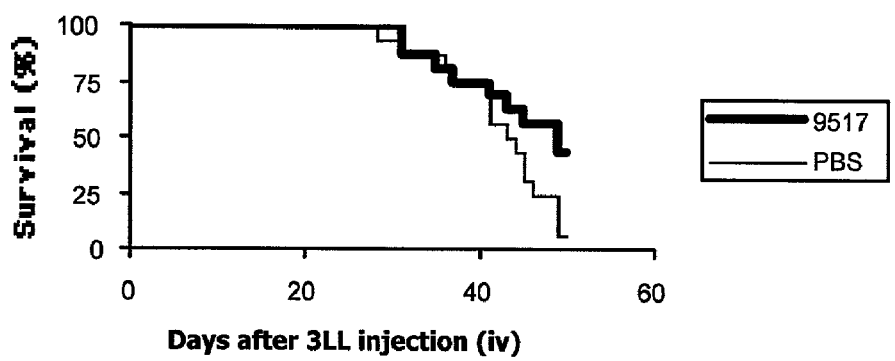
FIG. 9 is a graph showing the effect of treatment of mice with DS 9517.
Figure 10:
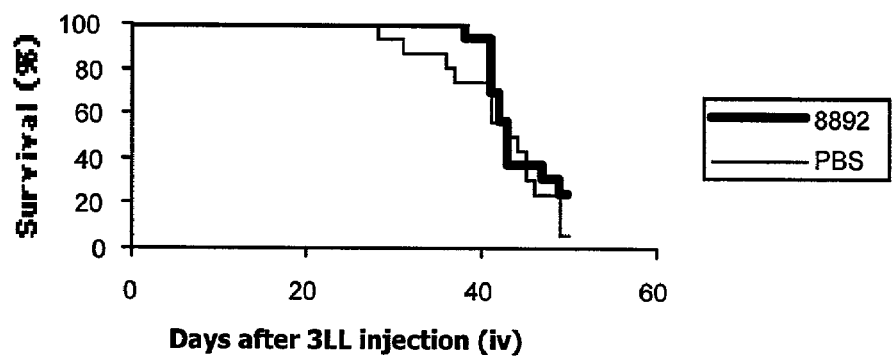
FIG. 10 is a graph showing the effect of treatment of mice with DS 8892.
Figure 11:
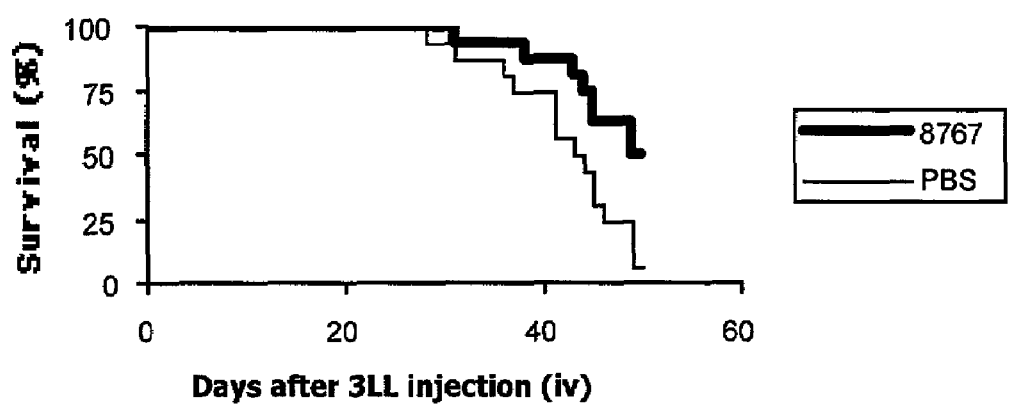
FIG. 11 is a graph showing the effect of treatment of mice with DS 8767.
Figure 12:
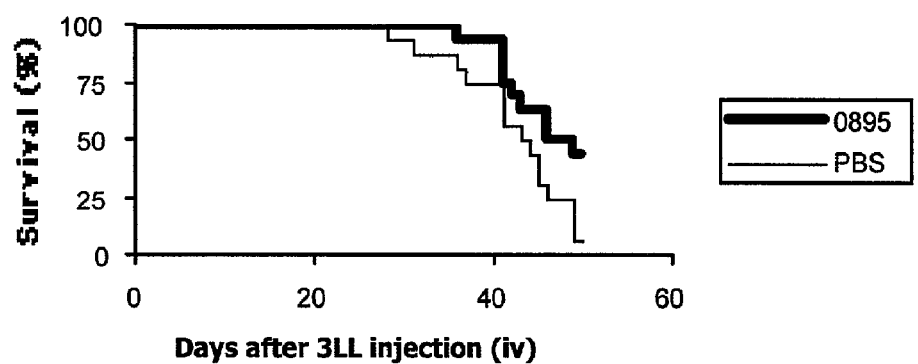
FIG. 12 is a graph showing the effect of treatment of mice with DS 0895.
Figure 13:
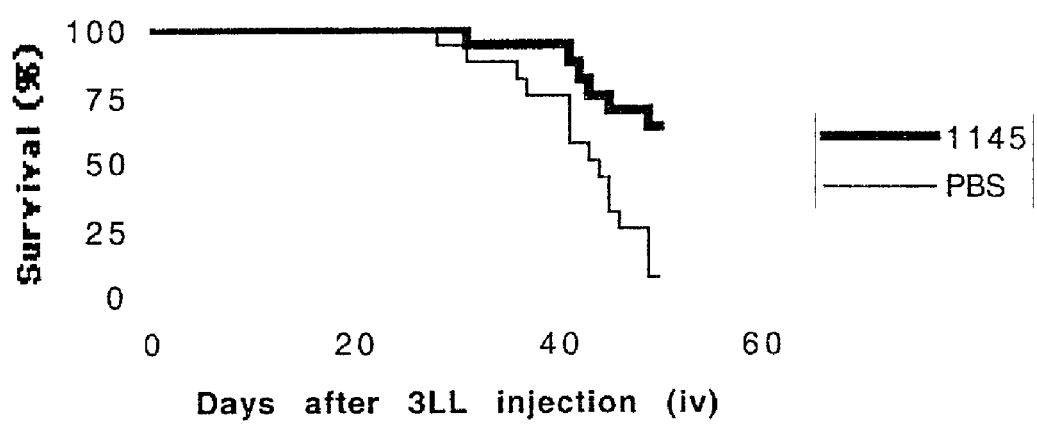
FIG. 13 is a graph showing the effect of treatment of mice with DS 1145.
Figure 14:
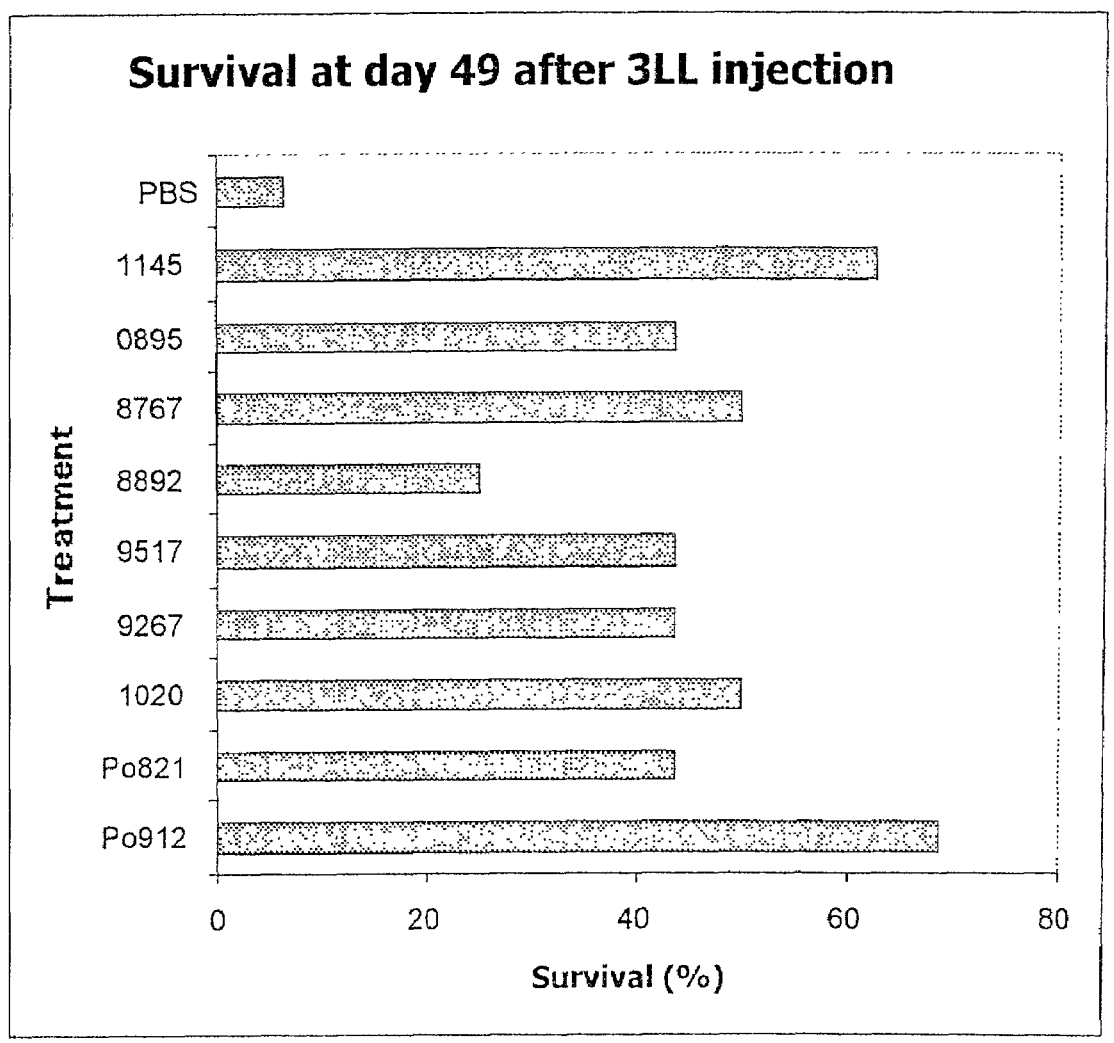
FIG. 14 is a graph showing comparative effects of the treatment of mice with different compounds at day 49 after injection with tumor cells.
Figure 15:
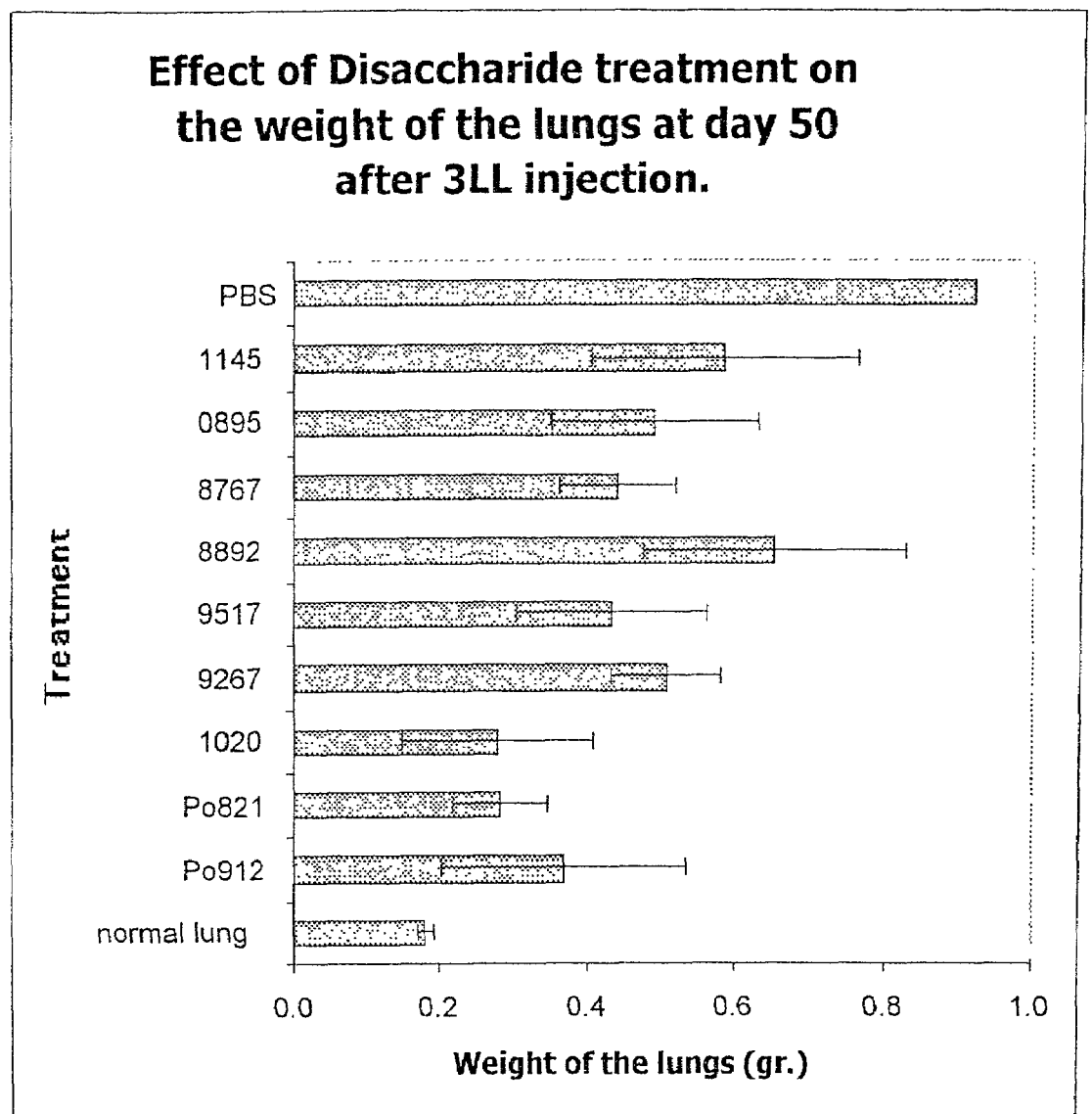
FIG. 15 is a graph showing comparative effects of the treatment of mice with different compounds on the weight of lungs.

Treatment with the different disaccharides, except for DS8892 (FIG. 10), resulted in a significant increase in the survival of the mice. Treatment with DS Po912 (FIG. 5) and DS 1145 (FIG. 13) appears to be the best treatment in terms of inhibition of mortality. DS Po912 increased significantly the mice survival to 68.75% from 6.2% (Table 1 and FIG. 14) and DS 1145 increased it to 62.6% (Table 1). DS 1020 (FIG. 7) and DS 8767 (FIG. 11) increased significantly the mice survival to 50% from 6.2% (Table 1 and FIG. 14). DS Po821 (FIG. 6), DS 9267 (FIG. 48), DS 9517 (FIG. 9) and DS 0895 (FIG. 12) significantly increased survival of the mice to 43.75% (Table 1 and FIG. 14).

In addition to measuring survival, some mice were sacrificed on day 50 and their lungs were examined and weighted. Increase in lung weight is a sign for tumor development; the heavier the lungs, the greater the amount of metastasis. The results, shown in Table 2, shows a substantially decrease in lung weight in mice receiving the treatment of DS Po821, DS 1020 and DS Po912.

Discussion

The best anti-tumor treatment was seen with DS Po912 as well as all the other tested DS, although to a lesser degree. In contrast, DS 8892 did not inhibit the tumor development at all. Without wishing to be limited to a single hypothesis, since the DS treatment was at the very early stage of development of the experimental metastasis, the DS may modulate the homing and tissue localization of tumor cells.

EXAMPLE 3

Methods and Compositions for Administration

The compounds according to the present invention, and their pharmaceutically acceptable salts, hereinafter referred to as the "therapeutic agents of the present invention", can be administered to a subject by various ways, which are well known in the art.

Hereinafter, the term "subject" refers to the human or lower animal to whom the therapeutic agent is administered. For example, administration may be done topically (including opthalmically, vaginally, rectally, intranasally and by inhalation), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to the therapeutic agent. Persons of ordinary skill in the art can easily determine optimum dosages, dosing methodologies and repetition rates.

Optionally, the therapeutic agent of the present invention is administered in an amount in a range of from about 1 to about 1000 μg of the agent per Kg of subject, weight per weight.

The following example is an illustration only of a method of treating a malignancy with the therapeutic agent of the present invention, and is not intended to be limiting.

The method includes the step of administering a therapeutic agent, in a pharmaceutically acceptable carrier, to a subject to be treated. The therapeutic agent is administered according to an effective dosing methodology, preferably until a predefined endpoint is reached, such as the absence of a symptom of the malignancy in the subject, and/or the prevention of the appearance of such a symptom in the subject, and/or the reduction of the number of metastatic malignant cells in the subject, and/or the prevention of the genesis of metastatic tumors.

Examples of tumors for which such a treatment would be effective include, but are not limited to, breast cancers such as infiltrating duct carcinoma of the breast or other metastatic breast cancers, lung cancers such as small cell lung carcinoma, bone cancers, bladder cancers such as bladder carcinoma, rhabdomyosarcoma, angiosarcoma, adenocarcinoma of the colon, prostate or pancreas, or other metastatic prostate or colon cancers, squamous cell carcinoma of the cervix, ovarian cancer, malignant fibrous histiocytoma, lymphoma and leukemia, skin cancers such as malignant melanoma, leiomyosarcoma, astrocytoma, glioma and heptocellular carcinoma.

It will be appreciated that the above descriptions are intended only to serve as examples, and that many other embodiments are possible within the spirit and the scope of the present invention.

Tables

TABLE 1

Survival at day 49 after 3LL injection

| DS | live mice | dead mice | survival (%) * | p-value |
|---|---|---|---|---|
| DS Po912 | 11 | 5 | 68.75 | 0.0003 |
| DS Po821 | 7 | 9 | 43.75 | 0.014 |
| DS 1020 | 8 | 8 | 50 | 0.005 |
| DS 9267 | 7 | 9 | 43.75 | 0.014 |
| DS 9517 | 7 | 9 | 43.75 | 0.014 |
| DS 8892 | 4 | 12 | 25 | 0.14 |
| DS 8767 | 8 | 8 | 50 | 0.005 |
| DS 0895 | 7 | 9 | 43.75 | 0.014 |
| DS 1145 | 10 | 6 | 62.5 | 0.0008 |
| PBS (control) | 1 | 15 | 6.2 | |

* survival (%) = [live mice/total mice] × 100

TABLE 2

Weights of lungs at day 50 after 3LL injection

| Treatment with DS | Weights ± SD (gr.) | Decrease (%) * |
|---|---|---|
| DS Po912 | 0.37 ± 0.17 | 60.1 |
| DS Po821 | 0.28 ± 0.07 | 69.3 |
| DS 1020 | 0.28 ± 0.13 | 69.8 |
| DS 9267 | 0.51 ± 0.07 | 44.8 |
| DS 9517 | 0.43 ± 0.13 | 53.0 |
| DS 8892 | 0.66 ± 0.18 | 28.8 |
| DS 8767 | 0.44 ± 0.08 | 52.2 |
| DS 0895 | 0.49 ± 0.14 | 46.7 |
| DS 1145 | 0.59 ± 0.18 | 36.4 |
| PBS | 0.92 | |

* Decrease (%) = [1−(weights of treated group/weights of control group)] × 100

Appendix of Structures

List of Heparin and Heparan sulfate Disaccharides

Po912
Sigma H 9392, (α-ΔUA-2S-[1→4]-GlcNS), produced by the action of heparinase I and II on heparin.

Po821
Our novel DS, Synthetic, (GlcNS,6S-[1→4]-GlcA-2S), produced by the action of heparanase on heparan sulfate.

DS 1020
Sigma H 1020, (α-ΔUA-[1→4]-GlcNS-6S), produced by the action of heparinase II on heparin.

DS 9267
Sigma H 9267, (α-ΔUA-2S-[1→4]-GlcNS-6S), produced by the action of heparinase I and II on heparin.

DS 9517
Sigma H 9517, (α-ΔUA-2S-[1→4]-GlcNAc-6S), produced by the action of heparinase II on heparin.

DS 8892,
Sigma H 8892, (α-ΔUA-2S-[1→4]-GlcN-6S), produced by the action of heparinase on heparin.

DS 8767
Sigma H 8767, (α-ΔUA-2S-[1→4]-GlcNAc), produced by the action of heparinase II on heparin.

DS 0895
Sigma H 0895, (α-ΔUA-[1→4]-GlcNAc), produced by the action of heparinase II and III on heparin.

DS 1145
Sigma H 1145, (α-ΔUA-[1→4]-GlcNS), produced by the action of heparinase II and III on heparin.

Abbreviation:
ΔUA = 4-deoxy-L-threohex-4-enopyranosyluronic acid.
GlcA = β-D-glucopyranoside uronic acid.
GlcN = D-glucosamine.
Ac = Acetyl.
NS, 2S, 6S, = N-sulfo, 2-sulfate and 6-sulfate respectively.

What is claimed is:

1. A method for treating a malignancy selected from the group consisting of breast cancer, lung cancer, bone cancer, bladder cancer, rhabdomyosarcoma, angiosarcoma, adenocarcinoma, prostate cancer, colon cancer, squamous cell carcinoma of the cervix, ovarian cancer, malignant fibrous histiocytoma, skin cancer, leiomyosarcoma, astrocytoma, glioma and heptocellular carcinoma in a subject;
   wherein the method comprises administering a pharmaceutically effective amount of a therapeutic agent to the subject, said therapeutic agent comprising an oligosaccharide, wherein said oligosaccharide has a molecular weight of less than about 3000 daltons and comprises a disaccharide of formula (I) or its pharmaceutically acceptable salt:

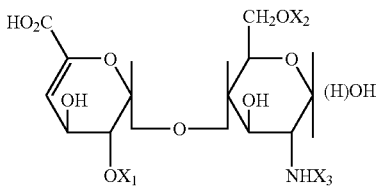

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates.

2. The method of claim 1, wherein said oligosaccharide is an N-sulfated-4-deoxy-4-en-iduronoglucosamine having at least one other sulfate group and pharmaceutically acceptable salts thereof.

3. The method of claim 1, wherein said oligosaccharide is an N-acetylated-4-deoxy-4-en-iduronoglucosamine having at least two sulfate groups and pharmaceutically acceptable salts thereof.

4. The method of claim 1, wherein said oligosaccharide is a disaccharide of formula (I) or its pharmaceutically acceptable salt:

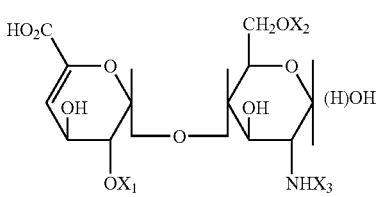

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates.

5. The method of claim 1, wherein said oligosaccharide is an N-sulfated-4-deoxy-4-en-glucuronoglucosamine having at least one other sulfate group or a pharmaceutically acceptable salt thereof.

6. The method of claim 1, wherein said oligosaccharide is a sulfated disaccharide.

7. The method of claim 1, wherein said oligosaccharide is a sulfated disaccharide.

8. The method of claim 1, wherein said oligosaccharide comprises at least one of Po912, DS 1145, DS 1020, DS 8767, Po821, DS 9267, DS 9517 and DS 0895.

9. The method of claim 8, wherein said oligosaccharide comprises Po912.

10. The method of claim 1, wherein the malignancy is a metastatic tumor.

11. The method of claim 1, wherein the malignancy is lung cancer.

12. The method of claim 1, wherein said oligosaccharide is administered in an amount in a range of from about 1 to about 1000 micrograms of oligosaccharide per Kg of subject, weight per weight.

13. The method of claim 1, wherein said cancer is metastatic.

14. The method of claim 13, wherein said oligosaccharide is a sulfated glucosamine derivative and pharmaceutically acceptable salts thereof.

15. The method of claim 14, wherein said oligosaccharide is a sulfated disaccharide.

16. The method of claim 13, wherein said oligosaccharide is an N-acetylated-4-deoxy-4-en-iduronoglucosamine having at least two sulfate groups and pharmaceutically acceptable salts thereof.

17. The method of claim 15, wherein said oligosaccharide is a disaccharide of formula (I) or its pharmaceutically acceptable salt:

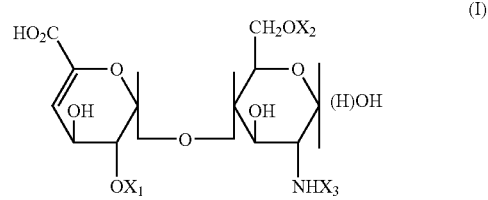

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates.

18. The method of claim 15, wherein said oligosaccharide is an N-sulfated-4-deoxy-4-en-glucuronoglucosamine having at least one other sulfate group or a pharmaceutically acceptable salt thereof.

19. The method of claim 12, wherein said oligosaccharide comprises at least one of Po912, DS 1145, DS 1020, DS 8767, DS Po821, DS 9267, DS 9517 and DS 0895.

20. The method of claim 13, wherein said oligosaccharide comprises at least one of Po912, DS 1145, DS 1020, DS 8767, Po821, DS 9267, DS 9517 and DS 0895.

21. The method of claim 20, wherein said oligosaccharide comprises Po912.

22. The method of claim 19, wherein said oligosaccharide is DS 1145.

23. The method of claim 13, wherein said oligosaccharide alters localization of tumor cells to treat the metastatic cancer.

24. The method of claim 13, wherein said oligosaccharide alters homing activity of tumor cells to treat the metastatic cancer.

25. The method of claim 13, wherein said oligosaccharide interferes with the CXCR4 7TM-GPCR signaling pathway.

26. The method of claim 1, wherein said oligosaccharide has a molecular weight lying in the range of from about 400 daltons to about 2000 daltons.

27. The method of claim 26, wherein said oligosaccharide has a molecular weight lying in the range of from about 400 to about 1100 daltons.

28. The method of claim 1, wherein said malignancy is selected from the group consisting of breast cancer, bone cancer, bladder cancer, rhabdomyosarcoma, angiosarcoma, adenocarcinoma, prostate cancer, colon cancer, squamous cell carcinoma of the cervix, ovarian cancer, malignant fibrous histiocytoma, skin cancer, leiomyosarcoma, astrocytoma, glioma and heptocellular carcinoma.

* * * * *